US005728404A

United States Patent [19]
von Rheinbaben et al.

[11] Patent Number: 5,728,404
[45] Date of Patent: Mar. 17, 1998

[54] VIRUCIDAL DISINFECTANT

[75] Inventors: Friedrich von Rheinbaben, Duesseldorf; Klaus-Peter Bansemir, Langenfeld; Beate Mainz, Marburg; Klaus Hachmann, Hilden, all of Germany

[73] Assignee: Henkel Kommanditgesellschaft auf Aktien, Duesseldorf, Germany

[21] Appl. No.: 295,726

[22] PCT Filed: Feb. 17, 1993

[86] PCT No.: PCT/EP93/00384

§ 371 Date: Oct. 31, 1994

§ 102(e) Date: Oct. 31, 1994

[87] PCT Pub. No.: WO93/16597

PCT Pub. Date: Sep. 2, 1993

[30] Foreign Application Priority Data

Feb. 26, 1992 [DE] Germany .................. 42 05 828.7

[51] Int. Cl.⁶ .................. A61K 31/045; A61K 31/28; A61K 31/315

[52] U.S. Cl. .................. 424/642; 424/600; 424/617; 424/641; 424/643; 514/494; 514/724; 514/739

[58] Field of Search .................. 424/618, 619, 424/641, 642, 643, 600, 617; 514/724, 494, 739

[56] References Cited

U.S. PATENT DOCUMENTS

| | | | |
|---|---|---|---|
| Re. 33,465 | 11/1990 | Eby, III | 514/494 |
| 2,118,225 | 5/1938 | Pierce | 424/685 |
| 4,198,296 | 4/1980 | Doumas et al. | 210/668 |
| 4,407,818 | 10/1983 | Lionelle et al. | 514/494 |
| 5,043,357 | 8/1991 | Hoffler et al. | 514/553 |
| 5,208,031 | 5/1993 | Kelly | 424/614 |
| 5,429,819 | 7/1995 | Oka et al. | 424/400 |
| 5,645,846 | 7/1997 | Oka et al. | 424/405 |

FOREIGN PATENT DOCUMENTS

| | | |
|---|---|---|
| 0381522 | 8/1989 | European Pat. Off. . |
| 1642001 | 4/1971 | Germany . |
| 2608408 | 11/1976 | Germany . |

OTHER PUBLICATIONS

Grossgebauer, K., "Disinfection", *Marcel Dekker, Inc.*, New York, New York, M.A. Benarde .ed., 1970, pp.. 103–148.
Block, S., "Disinfection, Sterilization, and Preservation", *Principles of Viral Control and Transmission*,Lea & Febiger, Philadelphia, 1991, 4th edition, pp–438–444.
Chemical Abstracts 115 (20):214973m (1991).
Chemical Abstracts 94(16):127395d (1980).

*Primary Examiner*—John Pak
*Attorney, Agent, or Firm*—Wayne C. Jaeschke; John Daniel Wood; Daniel S. Ortiz

[57] ABSTRACT

Methods of virucidal disinfection with virucidal disinfectants containing an active quantity of salts of metals of the alkaline earth metals, alkali metals, earth metals and/or metals of the first, second or third secondary group of the periodic system of elements in the form of a solution in water and/or alcohol are provided. The virucidal activity of alcohols or alcohol/water mixtures with a total alcohol concentration of 40 to 90% and preferably 50 to 80% can be considerably increased by addition of base- or acid-hydrolyzed salts of metal ions of the earth metal and meta metal group of the periodic system of elements in quantities of 0.1 to 1% by weight and preferably in quantities of 0.2 to 0.6% by weight. Normally ineffectual alcohol mixtures or alcohol/water mixtures thus develop far-reaching virucidal activity. The disinfectants may also contain small quantities of substances for improving compatibility with the skin, wetting agents and corrosion inhibitors.

7 Claims, No Drawings

VIRUCIDAL DISINFECTANT

This application is a 371 of PCT/EP93/00384, filed on Feb. 17, 1993.

BACKGROUND OF THE INVENTION

1. Field of the Invention

This invention relates to virucidal disinfectants, more particularly for hands.

2. Discussion of Related Art

Bacteria, fungi and the envelope bacteria which are relatively easy to inactivate (for example the AIDS and hepatitis B virus) are destroyed by many known hand disinfectants (cf. VII. Liste der nach den Richtlinien der Deutschen Gesellschaft für Hygiene und Mikrobiologie geprüften Desinfektionsverfahren (VIIth List of the Disinfection Processes Tested under the Guidelines of the German Society for Hygiene and Microbiology), Stand 31.3.1987, mhp-Verlag Wiesbaden, 1987).

However, these disinfectants have generally proved to be ineffective against envelope-free hydrophilic viruses and, in some cases, against envelope-free mildly lipophilic viruses such as, for example, entero-/picorna- or adeno- and reo viruses cf. Schoenemann et al.: Viruzide Wirkung von 30 H andedesinfektionsmitteln aus der VII. Liste der DGHM. (Virucidal Effect of 30 Hand Disinfectants from the VIIth List of the DHGM), Hyg.+Med. 14, 279–282 (1987)).

In general, therefore, important viruses of relevance in human medicine such as, for example, entero, polio, hepatitis A, ECHO, Coxsackie, corona, calici or rhino viruses cannot be adequately eliminated by known hand disinfectants. This fact can lead to the transmission of virus infections, particularly in hospitals, through contamination of the hands of patients and staff and the instruments used by them. There is also a danger of infection from contaminated surfaces.

Accordingly, the problem addressed by the present invention was to provide a virucidal disinfectant which could be used universally, but especially for hands.

It is known that pure methanol, ethanol, n-propanol, isopropanol or butanol have a distinct but limited virucidal effect in very high concentrations of around 80% or more. Against envelope-free hydrophilic viruses, this virucidal effect decreases with increasing chain length or decreasing hydrophilicity of the alcohols (Noda et al.: Virucidal Activity of Alcohols, J. Jap. Ass. Infect. Dis. 55, 355–366 (1981)). Lower concentrations of these alcohols are not sufficiently effective. Individually, pure propanol, isopropanol or butanol is definitely not sufficiently active against envelope-free hydrophilic viruses. Known mixtures of ethanol and isopropanol with a total active-substance content of 20 to 40% show no virucidal activity either.

The virucidal activity of metal salts, particularly zinc salts, has never been described before. Hitherto, virucidal activity as a disinfectant has only been claimed for lithium dodecyl sulfate in combination with a special nonionic surfactant dissolved in an aliphatic alcohol (EP 0 263 864 B1). Through its specificity, this combination does not concern the present invention.

SUMMARY OF THE INVENTION

The present invention relates to a virucidal disinfectant containing an active quantity of salts of metals of the alkaline earth metals, alkali metals, earth metals and/or metals of the first, second or third secondary group of the periodic system of elements in the form of a solution in water and/or alcohol.

DETAILED DESCRIPTION OF THE INVENTION

More particularly, it has been found that the virucidal activity of alcohols or alcohol/water mixtures with a total alcohol concentration of 40 to 90% and preferably 50 to 80% can be considerably increased by addition of base- or acid-hydrolyzed salts of metal ions of the earth metal and meta metal group of the periodic system of elements in quantities of 0.1 to 1% by weight and preferably in quantities of 0.2 to 0.6% by weight. Preferred anions of these salts are the strong inorganic acids and the weak organic acids. The corresponding hydrate salts may also be used. Normally ineffectual alcohol mixtures or alcohol/water mixtures thus develop far-reaching virucidal activity. The disinfectants may also contain small quantities of substances for improving compatibility with the skin, wetting agents and corrosion inhibitors.

Suitable alcohols are methanol, ethanol, n-propanol, isopropanol, butanol. Their concentration in aqueous solution is from 40% to 90% and preferably from 50% to 80%. Mixtures of ethyl alcohol and isopropyl alcohol in a ratio by weight of 8:1 to 1:1 are particularly effective.

The disinfectants according to the invention contain metals salts as an important component. In the context of the invention, metal salts are understood to be metal salts which are soluble in the preparations according to the invention. It is preferred to use solutions of metal salts, main group elements, such as aluminium, gallium, indium, and secondary group elements, such as scandium, yttrium, lanthanum, the lanthanides and also copper, silver, gold and zinc, cadmium, mercury.

Among the salts mentioned, salts of lanthanum, silver, zinc, cerium and aluminium are particularly preferred.

Providing the solubility requirement mentioned above is satisfied, the expert is free in the choice of the salt, i.e. in a first embodiment of the invention, salts of inorganic acids, for example chlorides, sulfates or nitrates, may be used.

In another embodiment of the invention, however, salts of organic acids, more particularly salts of monocarboxylic acids preferably containing no more than 6 carbon atoms, dicarboxylic acids, monohydroxycarboxylic acids or polyhydroxycarboxylic acids, may also be used. For example, it has proved to be particularly favorable for the purposes of the invention to use lactates, more particularly lactates of aluminium or silver.

The disinfectants according to the invention may be made up in the forms typical of disinfectants. Solutions sprayable by spray pumps or from aerosol cans have been successfully used for many disinfection problems. However, the disinfectants may also be made up in the form of gels or the like.

EXAMPLES

Virucidal activity was determined in accordance with the guidelines for testing virucidal disinfectants in human medicine (suspension test) (cf. Bundesgesundheitsamt Berlin: Guidelines of Bundesgesundheitsamt (BGA; German Federal Health Office) and Deutsche Vereinigung zur Bek ämpfung der Viruskrankheiten e.V. (DVV; German Association for the Control of Virus Diseases) for Testing the Effectiveness of Chemical Disinfectants Against Viruses, Zbl. Hyg. 189, 554–562 (1990)) because there have hitherto been no recognized processes in human medicine for virucidal testing on surfaces, instruments or the skin.

Example 1

50% by weight of ethanol
30% by weight of isopropanol
1% by weight of zinc chloride
Remainder water

Example 2

70% by weight of ethanol
1% by weight of zinc chloride
Remainder water

Example 3

60% by weight of ethanol
20% by weight of isopropanol
0.5% by weight of zinc chloride
Remainder water

Example 4

50% by weight of ethanol
30% by weight of isopropanol
0.5% by weight of zinc sulfate (or lanthanum nitrate hexahydrate, cerium chloride hexahydrate, aluminium lactate, silver lactate)
Remainder water The mixtures according to the preceding Examples were tested against polio, adeno, vaccinia and SV40 tumor virus in accordance with the DVV guidelines with and without additional protein loading. To this end, virus/disinfectant mixtures containing polio, adeno, vaccinia and SV40 tumor virus were incubated in the suspension test—contact time 5 minutes—on the one hand without additional protein loading and on the other hand with additions of 0.2% of bovine serum albumin and 10% of calf serum and titrated out on permissive tissue culture cells. The in-use concentration of the model formulations was 80 to 90% according to the method applied. Under the DVV guidelines, a reduction in the virus titer of at least 99.99% (equal to 4 powers of ten) is regarded as a satisfactory result.

Where 40 to 80% by weight ethanol, n- and isopropanol or butanol were used, it was not possible in the virus suspension test under the DVV guidelines to achieve adequate effectiveness against any of the four test viruses. A general reduction in the virus titer by >4 powers of ten was not obtained.

Ethanol/propanol mixtures (n and iso) showed equally poor activity in the DVV virus suspension test: against polio virus, the reduction in the virus titer produced by a mixture of 60% by weight of ethanol and 20% by weight of isopropanol, remainder water, after a contact time of 5 minutes was at most 2.3 powers of ten.

Against polio virus, aqueous solutions of 0.1 to 1% by weight of zinc chloride, zinc sulfate, lanthanum nitrate hexahydrate, cerium chloride hexahydrate, aluminium lactate or silver lactate also failed to produce any significant reduction in the virus titer after a contact time of 5 minutes.

We claim:

1. In a method of virucidal disinfection wherein a virus is contacted with an aqueous composition to inactivate the virus, the improvement comprising: contacting the virus with an aqueous virucidal disinfectant solution comprising water; 50% to 90% by weight of at least one member selected from the group consisting of $C_1$ to $C_4$ aliphatic monohydric alcohols; from 0.1% to 1.0% by weight of at least one zinc salt selected from the group consisting of zinc chloride, zinc nitrate and zinc sulfate; and optionally substances for improving compatibility with skin, wetting agents and corrosion inhibitors; wherein the virucidal activity of said aqueous virucidal disinfectant solution is improved over the virucidal activity of said aqueous virucidal disinfectant solution without said at least one zinc salt.

2. The method as claimed in claim 1 wherein said solution contains 0.2 to 0.6% by weight of said zinc salt.

3. The method as claimed in claim 1 wherein said solution contains at least one member selected from the group consisting of substances for improving compatibility with the skin, wetting agents and corrosion inhibitors.

4. The method as claimed in claim 1 wherein said solution contains 50 to 80% by weight of at least one member selected from the group consisting of $C_1$ to $C_4$ aliphatic monohydric alcohols.

5. The method as claimed in claim 1 wherein said at least one member selected from the group consisting of $C_1$ to $C_4$ aliphatic monohydric alcohols is a mixture of ethyl alcohol and isopropyl alcohol in a ratio by weight of 8:1 to 1:1.

6. The method of viricidal disinfection of claim 1, wherein the viricidal disinfectant comprises an aqueous solution containing 50 to 80% by weight of at least one $C_1$ to $C_4$ aliphatic alcohol and 0.1 to 0.6% by weight of said at least one zinc salt.

7. The method of claim 1 wherein the aqueous viricidal disinfectant solution comprises 0:1 to 1.0% by weight of said at least one zinc salt and at least one alcohol selected from the group consisting of ethanol, n-propanol and isopropanol.

* * * * *